United States Patent [19]

Hale

[11] Patent Number: 4,985,130
[45] Date of Patent: Jan. 15, 1991

[54] AMPEROMETRIC METHOD AND APPARATUS

[75] Inventor: John M. Hale, Meinier, Switzerland

[73] Assignee: Orbisphere Laboratories, Inc., Switzerland

[21] Appl. No.: 447,522

[22] Filed: Dec. 7, 1989

Related U.S. Application Data

[62] Division of Ser. No. 201,202, Jun. 1, 1988, Pat. No. 4,906,339.

[30] Foreign Application Priority Data

Jun. 5, 1987 [EP] European Pat. Off. ........ 87810325.8

[51] Int. Cl.$^5$ ............................................. G01N 27/40
[52] U.S. Cl. ................................ 204/415; 204/153.17; 204/400
[58] Field of Search ............... 204/400, 412, 415, 435, 204/153.1, 153.17

[56] References Cited

U.S. PATENT DOCUMENTS

| | | | |
|---|---|---|---|
| 3,208,926 | 9/1965 | Eckfeldt | 204/153.13 |
| 3,413,199 | 11/1968 | Morrow | 204/153.13 |
| 3,539,455 | 11/1970 | Clark | 204/408 |
| 3,629,089 | 12/1971 | Luck | 204/412 |
| 4,197,853 | 4/1980 | Parker | 204/412 |
| 4,315,753 | 2/1982 | Bruckenstein et al. | 204/406 |

FOREIGN PATENT DOCUMENTS

| | | |
|---|---|---|
| 0027005 | 4/1981 | European Pat. Off. . |
| 0122511 | 10/1984 | European Pat. Off. . |
| 0124818 | 11/1984 | European Pat. Off. . |
| 0205399 | 12/1986 | European Pat. Off. . |

Primary Examiner—T. Tung
Attorney, Agent, or Firm—Wigman & Cohen

[57] ABSTRACT

A method for determination of a first electroactive and normally gaseous species (EAGS) and a second EAGS in a fluid medium containing both EAGS; the medium is contacted with a first working electrode that is sensitive but to the first EAGS and generates a first amperometric signal that is indicative of the first EAGS concentration; the medium is also contacted with a second working electrode that is sensitive to both EAGS and produces a second amperometric signal that is indicative of the sum of both EAGS concentrations; the second EAGS concentration is calculated from the difference between the first and the second signal. For example, hydrogen can be measured in the presence of oxygen and this can be applied to monitor a fluid ambient or stream to prevent formation of explosive mixtures or corrosive conditions.

An apparatus suitable for use in the method may comprise two separate MEACS each having a generally conventional structure, or may be in the form of a novel integrated cell structure including at least two sensing electrodes and at least one counter electrode. This provides for safe and simple monitoring under differing ambient conditions and without critical impact of operating parameters such as membrane thickness.

9 Claims, 2 Drawing Sheets

AMPEROMETRIC METHOD AND APPARATUS

This is a divisional of co-pending application Ser. No. 07/201,202 filed on June 1, 1988 now U.S. Pat. No. 4,906,339.

CROSS-REFERENCE TO RELATED CASES

This application generally relates to subject matter disclosed in the following U.S. applications: Ser. No. 773,163, filed Mar. 1, 1977, issued as U.S. Pat. No. 4,096,047; Ser. No. 164,291, filed June 30, 1980, issued as U.S. Pat. No. 4,325,797; Ser. No. 319,708, filed Nov. 9, 1981, issued as U.S. Pat. No. 4,372,021; Ser. No. 345,536, filed Feb. 3, 1982, issued as U.S. Pat. No. 4,518,477; Ser. No. 493,316, filed May 10, 1983, issued as U.S. Pat. No. 4,563,249; Ser. No. 691,519, filed Jan. 14, 1985, issued as U.S. Pat. No. 4,585,542; Ser. No. 821,747, filed Jan. 23, 1986, issued as U.S. Pat. 4,711,703; Ser. No. 743,155, filed June 6, 1985; now abandoned Ser. No. 890,155, filed July 28, 1986, now U.S. Pat. No. 4,830,713; and Ser. No. 07/201,202, filed June 1, 1988, now U.S. Pat. No. 4,906,339.

BACKGROUND OF THE INVENTION (1) Field of the Invention

The invention generally relates to amperometry, i.e. the art of quantitative electroanalysis; specifically, the invention relates to an amperometric method for quantitative determination of a first electroactive and normally gaseous species (termed "EAGS"), such as elemental oxygen, and of a second electroactive and also normally gaseous species (the second "EAGS"), such as elemental hydrogen, in a normally fluid medium that may be gaseous or liquid.

(2) Description of the Prior Art

Reliable measuring or monitoring methods for determining the concentration of elemental hydrogen in the presence of oxygen are of importance wherever hydrogen is generated or used, e.g. in connection with electrolytical processes or when producing or reacting hydrogen in petrochemical or other operations because a gas mixture in which the fractions of oxygen and hydrogen exceed certain threshold limits of typically about 4% by volume may become explosive and may be dangerously unstable; this applies to mixtures of hydrogen and chlorine as well.

Determination of nitrous oxide in the presence of oxygen is another important problem within the ambit of the present invention.

Another problem of major importance is corrosiveness of water that is subjected to water-decomposing (i.e. oxygenolytic and hydrogenolytic) conditions such as, typically, exposure to radiolytic, e.g. neutronic, radiation. For example, the water used in water-moderated nuclear reactors is subject to radiolytic generation of oxygen and hydrogen but since the latter is relatively more "volatile" in such systems the oxygen concentration tends to increase and this, in turn, can be a cause for the water becoming corrosive to metallic components in contact therewith. One of the most effective methods to prevent such corrosiveness is the addition of elemental hydrogen in well-controlled quantities so that the hydrogen will act as a scavenger for the elemental oxygen.

Of course, amperometric methods for determining such EAGS individually, i.e. not in the same fluid or only after chemically or otherwise separating one from the other, are conventional, and membrane-enclosed amperometric cells (also termed "MEACs" for short) have been used for detection of either oxygen and hydrogen, notably since a simple and reliable hydrogen sensing method and apparatus have been disclosed by Applicant (cf. EP - A - 124,818).

Further, various methods of monitoring two substances or gases have been disclosed in French Patent No. 2,399,021 (corresponding with U.S. Pat. No. 4,197,853), U.S. Pat. No. 4,315,753 and in European Patent Application Nos. 122,511, 124,818 and 205,399.

However, insofar as amperometric determination of different EAGS is concerned, such methods tend to be rather complicated in that they involve chemical conversion or difficult and limiting operation requirements including specified membrane thicknesses and/or electrode operation at differing potentials. The last mentioned requirement is particularly undesirable for any routine-type measuring or monitoring application because changing the operating potential of a sensing electrode will introduce long delays because of the relative large capacitance of the sensing electrode and the time required for charging or discharging upon a change of the operating potential.

OBJECTS AND SUMMARY OF THE INVENTION

Accordingly, it is a main object of the invention to provide for an amperometric method capable of reliable yet simple quantitative determination of a first EAGS, such as elemental oxygen, and of a second EAGS, such as hydrogen, when both are present in one and the same fluid medium as explained above, while the medium contains the first species in a first concentration and the second species in a second concentration.

Another object of the invention is a method of the type just mentioned which is not limited to particular operational requirements including selection of membranes within a specified range of thickness and/or operation of the sensing electrode at differing potentials.

Another object of the invention is an apparatus including two membrane-enclosed amperometric cells for use in the said method.

Yet another object is a novel integral cell structure for use in the said method and including at least two sensing electrodes.

Further objects will become apparent as this specification proceeds.

It has been found according to a first embodiment of the invention that the above objects and further advantages will be achieved in an amperometric method for quantitative determination of a first electroactive and normally gaseous species, such as elemental oxygen, and of a second electroactive and normally gaseous species, such as elemental hydrogen, in a normally fluid medium, such as water, containing said first species in a first concentration and said second species in a second concentration; said medium being in a gaseous or liquid state, by (a) contacting said medium with a first and selective working electrode that is sensitive only to said first electroactive species to obtain a first amperometric signal that is indicative of said first concentration;

(b) contacting said medium with a second and non-selective working electrode that is sensitive to both the said first electroactive species as well as to said second electroactive species to obtain a second amperometric signal that is indicative of a sum of said first concentration and said second concentration;

(c) and determining said second concentration of said second electroactive species from a difference between said first amperometric signal and said second amperometric signal.

The above terms "normally gaseous" and "normally fluid" are used herein to indicate that a substance or phase of interest is gaseous or fluid when at normal ambient temperatures and pressures of typically about 20° C. and about 1 bar. The term "elemental" is intended to include elements both in a molecular or an atomic state but the invention is not restricted to elelemtal EAGS since a number of normally gaseous electroactive compounds, such as nitrous oxides, may be of interest as one of the EAGS in the inventive method.

The normally fluid medium may be a mixture of gases, such as air, or a process gas containing the first and the second EAGS, and may be at reduced, normal or elevated pressures and at temperatures within a typical range of from about −10° C. to about 95° C.; alternatively, the fluid medium may be a liquid, such as water that contains both the first and the second EAGS in a dissolved state.

Preferably, the medium is in "simultaneous", i.e. spatially close contact with the first and the second working electrode but this is not critical; according to a first embodiment, the inventive method can be worked with the two electrodes as the sensing electrodes of two different MEACS arranged at different positions in a conduit through which the medium is passed such that no appreciable differences of essential conditions, notably the concentrations of the EAGS, will be encountered at the differing positions of the MEACs; according to a second embodiment, the inventive method is worked with a new integrated type of MEAC which comprises both working electrodes and at least one counter electrode.

It has been found according to the invention that a satisfactory selectivity of the first working electrode only to the first species can be obtained if that working electrode (e.g. the cathode when oxygen is the first species) is made of an "amperometrically selective" metal as explained in more detail below, e.g. gold, silver, copper, or an alloy of these metals or even stainless steel and similar metals when oxygen is the first EAGS. Obviously, it is but the active or sensing surface of the working electrodes that need consist of such a selective metal. The second working electrode, or active surface thereof, is made of an "amperometrically unselective" metal as will be explained in more detail below, typically platinum, a platinum-group metal (Os, Ir, Pd, Rh, Ru) when the second EAGS is hydrogen.

According to a second embodiment the invention provides an apparatus for quantitative determination of a first and normally gaseous electroactive species and of a second electroactive and normally gaseous species in a fluid medium containing said first species in a first concentration and said second species in a second concentration, said apparatus comprising:

a first membrane-enclosed amperometric cell having a working electrode that is selectively sensitive but to said first electroactive species and a sensing face arranged within a containment means for holding or passing said medium; said first cell being capable of producing an amperometric signal that is indicative of said first concentration;

a second membrane-enclosed amperometric cell having a working electrode that is sensitive to both said first and said second electroactive species; said second cell having a sensing face arranged within said containment means; said second cell being capable of producing an amperometric signal that is indicative of a sum of said first and said second concentration;

and means for receiving said first amperometric signal and said second amperometric signal, and for generating an output signal that is indicative, at least, of said second concentration.

According to a further embodiment the invention provides an integrated cell for quantitative determination of a first and normally gaseous electroactive species and of a second electroactive and normally gaseous species in a fluid medium containing said first species in a first concentration and said second species in a second concentration, said cell comprising:

a first working electrode that is selectively sensitive only to said first electroactive species and is capable of producing an amperometric signal that is indicative of said first concentration;

a second working electrode that is sensitive to both said first and said second electroactive species and is capable of producing an amperometric signal that is indicative of a sum of said first and said second concentration;

at least one counter electrode for cooperation with at least one of said working electrodes, said working electrodes and said counter electrode being arranged within an electrolyte space for electrolytically connecting said working electrodes and said at least one counter electrode by means of an aqueous electrolyte; and a semi-permeable membrane covering said electrolyte space and permitting passage of said first and said second gaseous species but substantially preventing passage of said aqueous electrolyte.

BRIEF DISCUSSION OF THE PREFERRED EMBODIMENTS

According to a first preferred embodiment the inventive method is applied to monitoring of hydrogen concentrations in a gaseous medium so as to indicate, and preferably prevent, formation of a mixture known to be explosive.

According to a second preferred embodiment the inventive method is applied to monitoring of corrosion parameters, such as a relative deficiency of elemental hydrogen in the presence of elemental oxygen, in an aqueous medium that is exposed to radiolysis and, specifically, to oxygenolytic conditions, such as typically an aqueous moderator or processing liquid exposed to high-energy radiation, such as typically in the core of a nuclear reactor.

Preferably, the first working electrode for generating the first amperometric signal has a sensing surface made of a metal selected from gold, silver, copper and alloys of said metals, and stainless steel; also, it is preferred for many purposes if the second working electrode for generating the second amperometric signal has a sensing surface made of a metal selected from platinum, platinum-group metals and alloys thereof.

BRIEF DESCRIPTION OF THE DRAWINGS

The invention will now be explained in more detail with reference to the enclosed drawings in which.

DETAILED DESCRIPTION OF THE DRAWINGS

Figure 1:
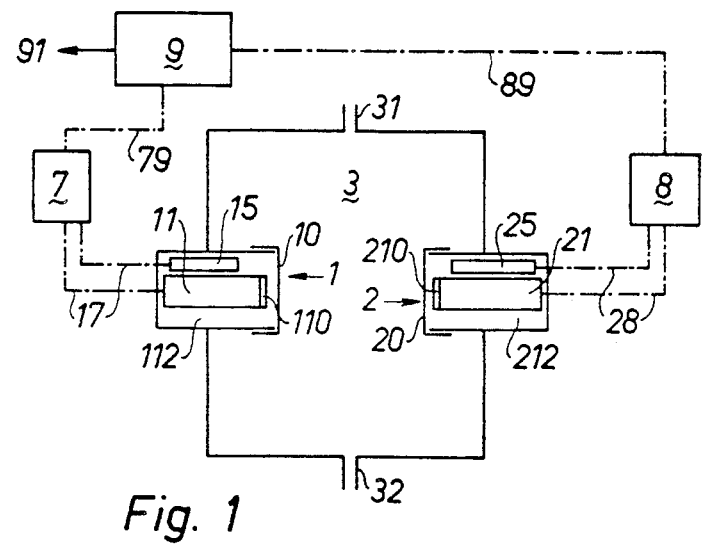
FIG. 1 is a diagrammatic illustration of an apparatus for carrying out the novel method.

The diagram of FIG. 1 shows a first MEAC 1 of a generally conventional structure as disclosed, for example, in U.S. Pat. No. 4,096,047 having a sensing face 10 exposed to a fluid medium provided within enclosure 3, a working electrode (e.g. cathode) 11 being made of Au, Ag, Cu or an alloy of these metals, or having its active surface 110 made of these metals. A counter electrode (e.g. anode) 15, e.g. of the conventional Ag/Ag-Cl-type, is arranged within the electrolyte space 112 containing a conventional electrolyte (not shown) while a constant DC-voltage is maintained between the counter electrode and the working electrode in a manner known per se. Additional electrodes, e.g. guard electrodes for the sensing or working electrode, may be used but are not shown. The sensing face 10 of MEAC 1 is provided by the surface of a conventional semi-permeable membrane, i.e. one that is substantially impermeable to the electrolyte but is permeable to the first EAGS, but a masked sensor as disclosed in EP - A - 205,399 is suitable as well and may be preferred if no guard electrode is to be used.

The second MEAC 2 has a structure similar to that of MEAC 1 except that the working electrode 21, or its active surface 210, is made of platinum, a platinum metal or an alloy of platinum group metals (platinum being considered to belong to the platinum group). The sensing face 20 of MEAC 2 again is a semipermeable membrane of the type known (e.g. as disclosed in EP - A - 124,818) and the sensing face 20 is exposed to the medium within enclosure 3. As shown, enclosure 3 may be provided with an inlet 31 and an outlet 32 both of which could also be the "ends" of a tubular enclosure 3 if the latter is a conduit or the like fluid-passing means. In other words, no particular diameters are critical for enclosure 3 and/or its feeding ends.

Leads 28 are provided between working electrode 21 and counter electrode 25 to carry the amperometric signal generated at the working electrode 21 by reaction of both the first and the second EAGS to control instrument 8. The resulting signals may then be evaluated by an operator or fed, via conduits 79 and 89, to an evaluating device that converts the signals from instruments 7, 8 into a readout, monitoring signal, printer or the like output indicated schematically as output 91. A result obtained by a human operator from the readings of instruments 7 and 8 would also be considered as an "output 91".

Figure 2:
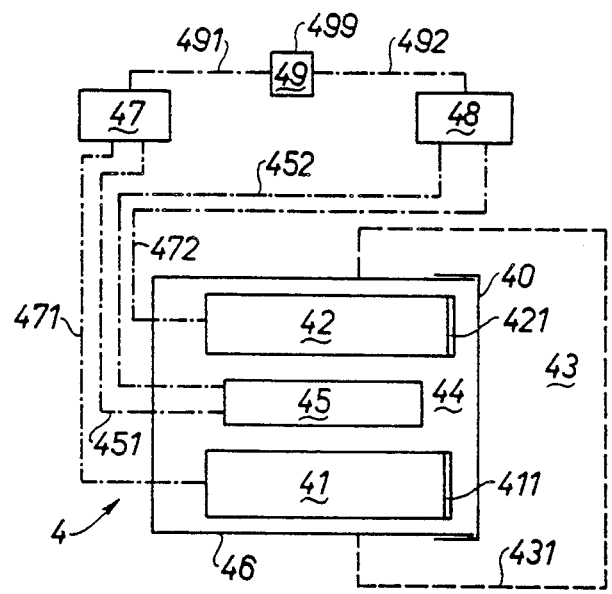
FIG. 2 is a diagrammatic illustration of a novel cell for use in the inventive method.

As diagrammatically shown in FIG. 2, the two MEACs 1, 2 of FIG. 1 can be integrated to form a new cell structure 4 comprising a first selective (e.g. for oxygen in the presence of hydrogen) working electrode 41 being made, or having an EAGS-exposed surface 411 made, for example, of Au, Ag, Cu, alloys thereof, or stainless steel, and a second non-selective working electrode 42 being made, or having an EAGS-exposed surface 421 made, for example, of Pt, another metal of the platinum group, or an alloy thereof.

At least one counter electrode 45 made, for example, of Ag/AgCl or another typical counter electrode material disclosed in the above mentioned U.S. Pat. No. 4,096,047, is provided within jacket 46 that encompasses an electrolyte space 44 covered by semi-permeable membrane 40 that permits passage of both EAGS contained in medium 43 but substantially prevents passage of the aqueous electrolyte that is contained in space 44.

A single counter electrode 45 may be used in which case it will serve as the counter electrode for, and cooperate with both, sensing electrodes 41, 42 to produce first and second amperometric signals 491, 492 as outputs from control instruments 47, 48 of a generally conventional type for use with MEACs.

Instrument 47 is connected with the first sensing electrode 41 and the counter electrode 45 via leads 451, 471, and the amperometric signal 471 produced by the first sensing electrode 41 with counter electrode 45 will be indicative but of the concentration of the first EAGS contained in the fluid medium 43 which, in turn, is optionally included by a container, conduit or the like containment means 431.

The amperometric signal 492 produced by the second sensing electrode 42 together with counter electrode 45 is indicative of the sum of the concentrations of both the first and the second EAGS in medium 43.

Since only one counter electrode 45 is used in the MEAC structure 4 of FIG. 2, each instrument 47, 48 will have an input lead 451, 452 connected with the one and only counter electrode 45 and an input lead 471, 472 from the first and the second sensing electrode, respectively. However, it is within the scope of the invention that each sensing electrode of an integrated cell as exemplified by FIG. 2 has a separate counter electrode (not shown).

Further, both in the separate cells 1, 2 of FIG. 1 as well as in the integrated cell 4 of FIG. 2, each sensing electrode and counter electrode could consist of several segments or portions, and guard electrodes or physical guards could be used in a manner known per se for all sensing electrodes.

Again, in FIG. 2, the outputs 491, 492 from instruments 47, 48 can be evaluated by a human operator or by an instrument 49 to produce, in either case, an output or signal 499 that is indicative of the difference of the amperometric signals produced by the two sensing electrodes and may, but need not, indicate the concentration of the second EAGS, or a derived parameter, such as a threshold value for indicating that explosive or corrosive conditions as explained above are approached and/or for triggering control or alarm signals to prevent that such conditions prevail.

DETAILED DISCUSSION OF PREFERRED EMBODIMENTS AND EXAMPLES

While specific examples will be given below, it is understood that they are presented but for illustration not limitation.

Example 1

For the embodiment of the invention where the EAGS contained in enclosure 3 (or 43) are oxygen (first EAGS) and hydrogen (second EAGS)—typically in mixture with inert gases such as nitrogen—and the selective working electrode surface 110 (or 411) is made of gold while the working electrode surface 210 (or 421) is made of platinum, electrode/EAGS-reactions are as follows:

When using an alkaline electrolyte, oxygen reacts at the selective electrode 11 or 41 or its surface 110 or 411 as follows:

$$O_2 + 2H_2O + 4e^- \rightarrow 4 OH^- \quad (1)$$

At the non-selective platinum electrode 21 or 42 or its surface 210 or 421 the above reaction occurs as well but hydrogen reacts as $$H_2 \rightarrow 2H^+ + 2e \quad (2)$$

Accordingly, the non-selective platinum electrode or surface simultaneously as a cathode in the oxygen reaction and as an anode in the hydrogen reaction. Since the electron flow through the platinum/electrolyte-interface is in opposite directions in the two reactions, the partial currents associated with the two reactions will cancel each other so that there will be a difference between the magnitudes of the electric currents measured with the two sensing electrodes. By combining these two currents the partial pressure of $O_2$ and $H_2$ in the sample stream can be calculated as explained in detail below. For simplicity, the sensors or sensing electrodes are assumed to operate in the manner of conventional MEACs or their respective working or sensing electrodes, that is to say, the magnitude of the current measured is limited by the rate of diffusion of the electroactive gases from the sample through the membrane to the electrode surface. In the case of electrode 21 or 42 this means that both reactions specified above must proceed very rapidly at the electrode surface 210 or 421, respectively. The conventional relation between current and partial pressure of the EAGS in a MEAC may be written as follows:

$$\text{Current} = \frac{\text{sensitivity per unit partial pressure}}{\text{times partial pressure}} \quad (3)$$

If the current is measured in microamperes and the partial pressure in kilopascals, the sensitivities will have units of microamperes per kilopascal. The symbol "i" is used for current, "S" for sensitivity and "p" for partial pressure; then, the relation may be written as follows:

$$i = S \cdot p \quad (4)$$

Generally, S will be dependent upon the temperature and the membrane. This relation is applied to the elective gold electrode surface with the following result:

$$i_g = S_{g,O2} \cdot p_{O2} \quad (5)$$

$$\text{Checksum} = (x_{O2}/y_{O2}) + (x_{H2}/y_{H2}) = 100\%$$

At the non-selective platinum electrode both of the cathodic and anodic reactions may be described in this way, so that the net current becomes:

$$x_{O2} = 100 \cdot p_{O2}/b = S_{p,O2} \cdot p_{O2} - S_{p,H2} \cdot p_{H2} \quad (6)$$

In order to use these relations for determination of the partial pressures of oxygen and hydrogen, the sensitivities $S_{g,O2}$, $S_{p,O2}$ and $S_{p,H2}$ must be determined. This is done by the following calibration procedure:

First, both MEACs 1 and 2 are, or MEAC 4 is, exposed to a gas stream containing a known fraction $y_{O2}$ of oxygen, but no hydrogen. Assuming that the stream passes the sensors at atmospheric pressure B, then the partial pressure $p_{O2}$ in this calibration medium by Dalton's law is:

$$p_{O2,1} = y_{O2} \cdot B \quad (7)$$

It follows from equation (5) that $$S_{g,O2} = i_{g,1}/p_{O2,1} = i_{g,1}/(y_{O2} \cdot B) \quad (8)$$

Furthermore, since $p_{H2} = 0$ in this calibration medium, it follows from equation (6) that $$S_{p,O2} = i_{p,1}/p_{O2,1} = i_{p,1}/(y_{O2} \cdot B) \quad (9)$$

Subsequently, MEACs 1+2 or 4 are exposed to a mixed gas stream containing known fractions of $O_2$ and $H_2$ in order to determine $S_{p,H2}$. This stream is conveniently prepared by bleeding into the $O_2$-containing stream used for $O_2$ calibrating a second stream containing a known fraction of $H_2$, $y_{H2}$ but no oxygen. Indicating by $i_{g,2}$ and $i_{p,2}$ the currents measured at MEACs 1+2 or 4 in this mixed stream: since $S_{g,O2}$ is known, the $O_2$ partial pressure in the stream can be calculated from equation (5)

$$p_{O2,2} = i_{g,2}/S_{g,O2} \quad (10)$$

Hence, the contribution to the total pressure represented by the original $O_2$ containing stream will be $$p_{O2,2}/Y_{O2} = i_{g,2}/(y_{O2} \cdot S_{g,O2}) \quad (11)$$

and that of the hydrogen containing stream will be:

$$B - i_{g,2}/(y_{O2} \cdot S_{g,O2}) \quad (12)$$

From this, the hydrogen partial pressure of the mixed stream results as:

$$p_{H2} = y_{H2} \cdot \{B - i_{g,2}/(y_{O2} \cdot S_{g,O2})\} \quad (13)$$

Returning to equation (6), the unknown term $S_{p,H2}$ can now be calculated as follows:

$$S_{p,H2} = \{S_{p,O2} \cdot i_{g,2}/S_{g,O2} - i_{p,2}\} \div \{y_{H2} \cdot [B - i_{g,2}/y_{O2} \cdot S_{g,O2}]\} \quad (14)$$

This completes the calibration procedure.

Example 2

The MEACs 1 and 2 were standard probes manufactured by Orbisphere Laboratories Geneva, i.e. Model 21152 having a gold cathode, and Model 2230 having a platinum electrode. The electrolyte used in both sensors contained 1 mol/lit potassium chloride and 1 mol/lit potassium hydroxide. A membrane TEFZEL (registered trademark DuPont) having a thickness of 25,4 micrometers was used on the platinum sensor (MEAC 2) and TEFZEL of 12,7 micrometers on MEAC 1. The voltage applied to both sensors was −0.6 volts (platinum or gold negative) versus the silver/silver chloride reference electrodes 15, 25.

Oxygen calibration was performed in pure $O_2$ ($y_{O2} = 1$). It was found that $$S_{g,O2} = 0.625 \; \mu A/kPa \text{ and } S_{p,O2} = 0.291 \; \mu A/kPa \quad (8\text{-}1)$$

The mixed $O_2$ and $H_2$ containing stream was prepared by bleeding pure $H_2$ ($y_{H2} = 1$) into the oxygen. Very low flow rates of only several ml/min were used. Then it turned out that:

$$S_{p,H2} = 0.494 \ \mu A/kPa \tag{14-1}$$

Once calibration had been completed, the fractions of $O_2$ and $H_2$ in the mixed stream were varied and the percentages of the constituent gases were calculated by application of equation (5) as:

$$x_{O2} = 100 \cdot p_{O2}/B = 100 \cdot i_g/B \cdot S_{g,O2} \tag{15}$$

and $$x_{H2} = (100/S_{p,H2} \cdot B)\{S_{p,O2} \cdot i_g/S_{g,O2} - i_p\} \tag{16}$$

The correctness of the measurement was checked in two ways. First, since the mixture is made from two component streams there should be a constant checksum:

$$\text{Checksum} = (x_{O2}/y_{O2}) + (y_{H2}/y_{H2}) = 100\% \tag{17}$$

Figure 3:
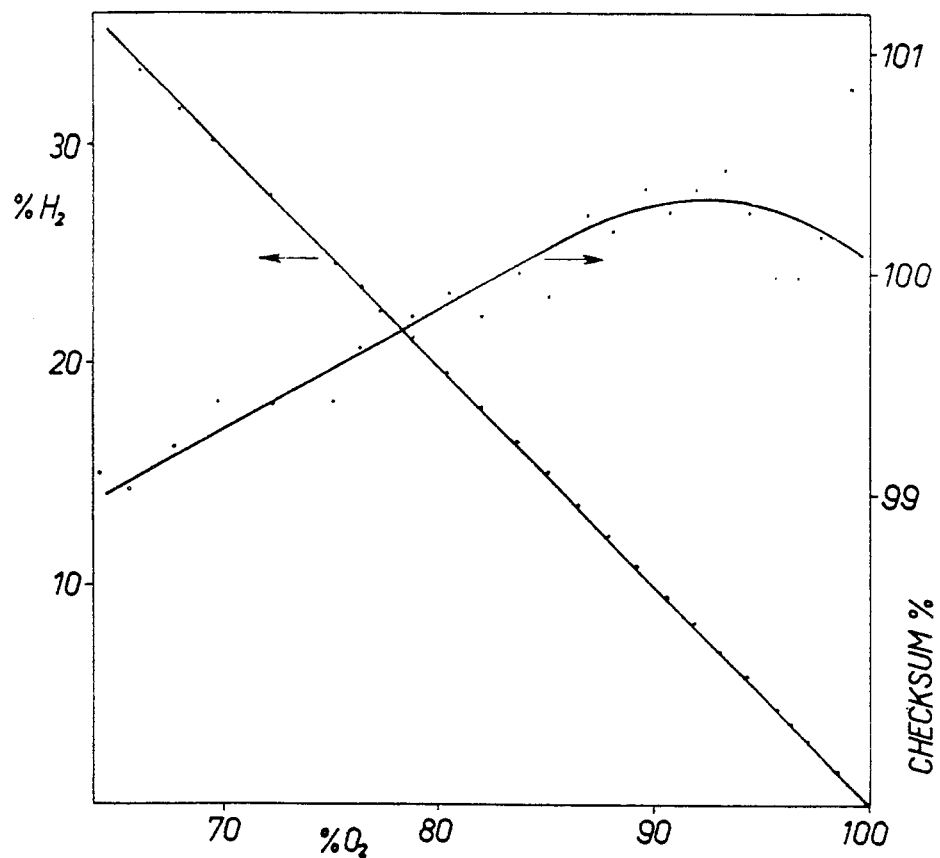
FIG. 3 is a diagram of a hydrogen/oxygen determination run according to a preferred example set forth in detail below and showing the hydrogen concentration in percent by volume on the ordinate and the oxygen concentration, again in percent by volume, on the abscissa for a series of testing fluids.

This was verified for all mixtures and the result is illustrated in FIG. 3. The rule is obeyed within 1% for all mixtures (0–35% $H_2$, 100–65% $O_2$) tested.

Secondly, combining equations (15), (16) and (17), it results that:

$$B \cdot y_{H2} \cdot S_{p,H2} + i_p = (i_g/S_{g,O2}) \cdot \{(y_{H2} \cdot S_{p,H2}/Y_{O2}) + S_{p,O2}\} \tag{18}$$

In the series of mixtures studied B, $y_{O2}$, $y_{H2}$, $S_{p,O2}$, $S_{g,H2}$ and $S_{p,O2}$ were all constant. Hence, the equation (18) is that of a straight line $$i_p = a + b \cdot i_g. \tag{19}$$

The correctness of this relation was also tested and found to be valid.

Example 3

In equations (5) and (6) different expressions were written for the currents measured at the gold and platinum electrodes 11, 12, respectively, even though assumed to be exposed to the same medium containing both oxygen and hydrogen. This comes about because the non-selective platinum electrode of MEAC 2 or 4 permits virtually instantaneous reaction of both hydrogen and oxygen at its surface 210/421, while the selective gold electrode 11 or 41 permits reaction but of oxygen. Thus, one can write an equation similar to (6) instead of (5) for the current at the gold cathode sensor but employing a sensitivity term $S_{g,H2}$ which is practically zero. In order to quantify the difference between the gold and platinum electrodes 11 or 41 and 21 or 42, a suitable equation was found as follows:

$$i = n \ F \ A_{p,H2}/[(1/k_e S_e) + (z_m/D_m S_m)] \tag{20}$$

and this supports the viability of the physicochemical basis of the inventive method.

The symbols used in equation (20) are defined as follows:

n=2=number of electrons participating in the oxidation electrochemical reaction of the second EAGS, e.g. hydrogen;
F=96,500 Coulombs per mole, the Faraday constant;
A=the area of the working electrode;
$p_{H2}$=the partial pressure of hydrogen in the medium;
$k_e$(cm/sec)=the rate constant of the hydrogen oxidation reaction;
$S_e$=the solubility of hydrogen dissolved in the electrolyte at the electrode surface;
$z_m$=the thickness of the membrane;
$D_m$=the diffusion coefficient of hydrogen in the membrane; and
$S_m$=the solubility of hydrogen in the membrane.

The given equation is best understood in terms of an electrical analog: by Ohm's law, the observed current "i" equals the voltage applied divided by the resistence to current flow encountered. The numerator of the equation is then analogous to the voltage, and the denominator analogous to the resistance. The numerator of equation (20), i.e. the resistance term $$R = (1/k_e S_e) + (z_m D_m S_m) \tag{21}$$

is of main interest. Its first term on the right hand side can be designated as the "resistance of the electrode reaction" and the second term can be designated as the "resistance of the membrane". It should be noted that this "resistance" is not the "electrical" resistance but rather the resistance to transport of the EAGS, e.g. hydrogen.

Hence, the difference between the selective and non-selective sensing electrodes used in the invention may be expressed as follows:

The "resistance" of the hydrogen oxidation reaction on electrode 21 or 42, e.g. having a platinum surface 210, is negligible in comparison with the "resistance" of the membrane 20 or 40, e.g. amounts to one percent of the latter "resistance" or less.

In contrast, the "resistance" of the electrode reaction on electrode 11 or 41, e.g. having a gold surface 110 or 411, exceeds by far the "resistance of the membrane 10 or 40, e.g. is a hundred times or more greater than the latter "resistance".

In practice, the magnitude of the membrane "resistance" can be determined, according to the present invention, because the term $(1/k_e S_e)$ is negligible for the non-selective electrode 21 or 42 (see equation 20) and the current delivered may be written as:

$$F A \ D_m \ S_m \ pH_2/z_m \tag{22}$$

Equations (13) and (14) provide for determination of the term $S_{p,H2}$ which, by comparison, is:

$$S_{p,H2} = F A \ D_m \ S_m/z_m \tag{23}$$

Since the area A of the sensing electrode is known or can easily be determined, it is possible to calculate directly the membrane resistance term $(z_m/D_m S_m)$ and for Example 2 $S_{p,H2}$ was determined as 0.494 $\mu$A/kPa since "A" of MEAC 2 was 0.3142 cm$^2$. Hence, the resistance term is as follows:

$$(z_m/D_m S_m) = 1.272 \cdot 10 \ cm^2 \cdot kPa \cdot S/mol.$$

With regard to MEAC 1 exposed to the same partial pressure of the second EAGS, e.g. $H_2$, tables can be used to determine the solubility thereof in its electrolyte; for hydrogen in pure water the solubility is approximately $7.5 \cdot 10^{-9}$ mol/(cm$^2 \cdot$kPa) at 25° C. The presence of salt in the electrolyte normally lowers the solubility in comparison with pure water but the effect is not large with normally used electrolyte compositions. Hence, the threshold magnitude of the electrode reaction rate constant can be calculated according to the invention as follows:

$$k_e^c = D_m S_m/z_m S_e = S_{p,H2}/n\, FAS_e \qquad (24)$$

and this permits classification of electrode metals into those suitable for non-selective electrodes of the non-selective electrode, i.e. sensitive to both the first and the second EAGS.

In the one class $$k_e >> k_e^c \qquad (24\text{-}1)$$

while in the other class $$k_e << k_e^c \qquad (24\text{-}2)$$

Reaction rate constants $k_e$ are not always tabulated while the "exchange current density" for the electrode reaction is given more frequently. The exchange current density $i_o$ is defined as the partial current for oxidation of hydrogen at the equilibrium potential (where the net current is zero), when the activity of hydrogen is unity ($p_{H2} = 100$ kPa). Thus:

$$i_o = 2\, F\, k_e^o S_e(p_{H2} = 100\ kPa) \qquad (25)$$

Where $k_e^o$ would be the value of the rate constant introduced earlier at the equilibrium potential. The rate constant varies with electrode potential in an exponential manner:

$$k_e = k_e\, exp(-\eta/b) \qquad (26)$$

wherein $\eta = V - V_o$ is the "overpotential" of the electrode V is the electrode potential and $V_o$ is the equilibrium potential b called the Tafel constant (J. Tafel, Z. Physik. Chem. 50, 641, 1905) which determines the steepness of the variation of rate constant with electrode potential.

Combining equations (24) and (28) the criterion for classification of electrode metals in terms of the exchange current can be expressed as:

$$i_o\, exp(\eta/b) = S_{p,H2}/A \qquad (27)$$

From the experimentally determined magnitude of $S_{p,H2}/A$ and the chosen value of the overpotential $\eta$ applied to the sensor, a critical or threshold value of the exchange current density can be evaluated for various possible values of the Tafel constant b. Tables can then be consulted to determine which metals (having $i_o >> i_o^c$) would be suitable for sensing both the first and the second EAGS.

For example, in the case of the preferred determination of hydrogen in the presence of oxygen according to the invention, a recent tabulation can be found in Chapter IX 2-3, "Hydrogen", by A. J. Appleby, H. Kita, M. Chemla and G. Bronoël, in "Encyclopedia of Electrochemistry of the Elements", edited by A. J. Bard, Volume IXA, Marcel Dekker, New York 1983, incorporated herein by reference.

Preferred electrodes for the selective sensing electrode 11 or 41 should have a sufficiently high exchange current for reduction of the first EAGS, e.g. oxygen, such that the rate of this process will be limited by the diffusion rate of the first EAGS through the membrane.

Various modifications of the above described specifics, e.g. regarding currents, electrolytes and suitable MEAC materials are apparent to one skilled in the amperometric art. For example, wherever "hydrogen" or "oxygen" or "chlorine" are mentioned herein, any isotopes thereof (deuterium, tritium etc.) are encompassed because the electrochemical behaviour depends upon the election shells of the elements in question. Further, "H2" and "O2" stand for "$H_2$" and "$O_2$" but so simplify printing.

The advantages of the present invention, as well as certain changes and modifications of the disclosed embodiments thereof, will be readily apparent to those skilled in the art. It is the Applicant's intention to cover by (their/his) claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that prior art allows.

What is claimed is:

1. An apparatus for quantitative determination of a first and normally gaseous electroactive species and of a second electroactive and normally gaseous species in a fluid medium containing said first species in a first concentration and said second species in a second concentration, said apparatus comprising:

a first membrane-enclosed amperometric cell having a working electrode that is selectively sensitive only to said first electroactive species and a sensing face arranged within a containment means for holding or passing said medium; said first cell being capable of producing an amperometric signal that is indicative of said first concentration; a second membrane-enclosed amperometric cell having a working electrode that is sensitive to both said first and said second electroactive species; said second cell having a sensing face arranged within said containment means; said second cell being capable of producing an amperometric signal that is indicative of a sum of said first and said second concentration; and means for receiving said first amperometric signal and said second amperometric signal, and for generating an output signal that is indicative, at least, of said second concentration;

wherein said first working electrode has a sensing surface made of gold and is operated with a counter electrode at a potential at which said sensing surface of said first working electrode is sensitive only to said first electroactive species; and wherein said second working electrode has a sensing surface made of a metal selected from platinum, platinum-group metals and alloys thereof and is operated with a counter electrode at a potential at which said sensing surface of said second working electrode is sensitive to both said first and second electroactive species.

2. An integrated cell for quantitative determination of a first and normally gaseous electroactive species and of a second electroactive and normally gaseous species in a fluid medium containing said first species in a first concentration and said second species in a second concentration, said cell comprising:

a first working electrode that is selectively sensitive only to said first electroactive species and is capable of producing an amperometric signal that is indicative of said first concentration; a second working electrode that is sensitive to both said first and second electroactive species and is capable of producing an amperometric signal that is indicative of a sum of said first and said second concentration; at least one counter electrode for cooperation with at least one of said working electrodes, said working electrodes and said counter electrode being arranged within an electrolyte space for electrolytically connecting said working electrodes and said at least one counter electrode by means of an aqueous electrolyte; and a semi-permeable membrane covering said electrolyte space and permitting passage of said first and said second gaseous species but substantially preventing passage of said aqueous electrolyte;

wherein said first working electrode has a sensing surface made of gold and is operated with a counter electrode at a potential at which said sensing surface of said first working electrode is sensitive only to said first electroactive species; and wherein said second working electrode has a sensing surface made of a metal selected from platinum, platinum-group metals and alloys thereof and is operated with a counter electrode at a potential at which said sensing surface of said second working electrode is sensitive to both said first and second electroactive species.

3. An amperometric apparatus for monitoring hydrogen concentration in a gaseous medium containing oxygen for preventing formation of an explosive mixture; comprising:

means for contacting said gaseous medium with a first and selective working electrode having a sensing surface made of gold and being operated with a counter electrode at a potential at which said sensing surface of said first working electrode is sensitive only to said oxygen to obtain a first amperometric signal that is indicative of said oxygen concentration;

means for contacting said gaseous medium with a second and non-selective working electrode having a sensing surface made of a metal selected from platinum, platinum-group metals and alloys thereof and being operated with a counter electrode at a potential at which said sensing surface of said second electrode is sensitive both to said oxygen as well as to said hydrogen to obtain a second amperometric signal that is indicative of a sum of said oxygen concentration and said hydrogen concentration;

means for determining said hydrogen concentration from a difference between said first amperometric signal and said second amperometric signal; and means, connected to said determining means, for evaluating whether said hydrogen concentration has a predetermined value indicating explosive conditions.

4. The apparatus of claim 3 further comprising means for additionally generating a warning signal if said hydrogen concentration exceeds a predetermined level.

5. Apparatus for monitoring a predetermined corrosion parameter based on oxygen and hydrogen concentration in an aqueous medium containing oxygen and hydrogen and exposed to radiolytic conditions; comprising:

means for contacting said aqueous medium with a first and selective working electrode having a sensing surface made of gold and being operated with a counter electrode at a potential at which said sensing surface of said first working electrode is sensitive only to oxygen to obtain a first amperometric signal that is indicative of a concentration of said oxygen in said aqueous medium;

means for contacting said aqueous medium with a second and non-selective working electrode having a sensing surface made of a metal selected from platinum, platinum-group metals and alloys thereof and being operated with a counter electrode at a potential at which said sensing surface of said second working electrode is sensitive to both oxygen as well as to hydrogen to obtain a second amperometric signal that is indicative of a sum of said oxygen and said hydrogen concentration in said aqueous medium;

means for determining said hydrogen concentration from a difference between said first amperometric signal and said second amperometric signal; and means, connected to said determining means, for evaluating whether said hydrogen concentration has a predetermined value indicating corrosive conditions.

6. The apparatus of claim 5 further comprising means for additionally generating a signal when said hydrogen concentration is below a level required to scavenge oxygen from said aqueous medium.

7. An amperometric apparatus for quantitative determination of elemental oxygen and of elemental hydrogen in a normally fluid medium containing said elemental oxygen in a first concentration and said elemental hydrogen in a second concentration; said medium being in a gaseous or liquid state; comprising:

means for contacting said medium with a first and selective working electrode that is sensitive only to elemental oxygen to obtain a first amperometric signal that is indicative of said first concentration;

means for contacting said medium with a second and non-selective working electrode that is sensitive both to elemental oxygen and elemental hydrogen to obtain a second amperometric signal that is indicative of a sum of said first concentration and said second concentration; whereby said second concentration of elemental hydrogen is determined from a difference between said first amperometric signal and said second amperometric signal;

wherein said first working electrode has a sensing surface made of gold and is operated with a counter electrode at a potential at which said sensing surface of said first working electrode is sensitive only to elemental oxygen; and wherein said second working electrode has a sensing surface made of a metal selected from platinum, platinum-group metals and alloys thereof and is operated with a counter electrode at a potential at which said sensing surface of said second working electrode is sensitive to both elemental oxygen and elemental hydrogen.

8. The apparatus of claim 7 wherein said medium is gaseous and further comprising means for monitoring said second concentration to indicate a threshold value of said second concentration for detecting formation of an explosive mixture of hydrogen and oxygen.

9. The apparatus of claim 7 wherein said medium is an aqueous fluid exposed to radiolytic radiation; and further comprising means for monitoring said second concentration to indicate a threshold value of said first concentration for detecting formation of a corrosive state of said aqueous fluid.

* * * * *